US012588816B2

(12) United States Patent
Schwaibold

(10) Patent No.: US 12,588,816 B2
(45) Date of Patent: Mar. 31, 2026

(54) TELEMONITORING IN RESPIRATION

(71) Applicant: Loewenstein Medical Technology S.A.,
Luxembourg (LU)

(72) Inventor: Matthias Schwaibold, Karlsruhe (DE)

(73) Assignee: Loewenstein Medical Technology S.A.,
Luxembourg (LU)

( * ) Notice: Subject to any disclaimer, the term of this
patent is extended or adjusted under 35
U.S.C. 154(b) by 1789 days.

(21) Appl. No.: 16/566,940

(22) Filed: Sep. 11, 2019

(65) Prior Publication Data

US 2020/0085303 A1      Mar. 19, 2020

(30) Foreign Application Priority Data

Sep. 14, 2018     (DE) .......................... 102018007256.9

(51) Int. Cl.
A61B 5/00         (2006.01)
A61M 16/00        (2006.01)
A62B 23/02        (2006.01)

(52) U.S. Cl.
CPC ....... A61B 5/0024 (2013.01); A61M 16/0003
(2014.02); A61M 16/0051 (2013.01); A62B
23/025 (2013.01)

(58) Field of Classification Search
CPC ..... A61B 5/0024; A61B 5/0022; A61B 5/002;
A62B 23/025; A61M 16/0051; A61M
16/0003
See application file for complete search history.

(56) References Cited

U.S. PATENT DOCUMENTS

| | | | | |
|---|---|---|---|---|
| 5,881,723 A * | 3/1999 | Wallace | .................. | G06F 9/453 |
| | | | | 128/204.23 |
| 2007/0221224 A1* | 9/2007 | Pittman | ............... | A61M 16/204 |
| | | | | 128/203.14 |
| 2007/0272242 A1* | 11/2007 | Sanborn | ................... | A61B 5/08 |
| | | | | 128/204.23 |
| 2010/0275921 A1* | 11/2010 | Schindhelm | ........... | G16H 40/67 |
| | | | | 600/533 |

(Continued)

FOREIGN PATENT DOCUMENTS

WO          2018083711 A1     5/2018

*Primary Examiner* — Joseph D. Boecker
*Assistant Examiner* — Brian T Khong
(74) *Attorney, Agent, or Firm* — Abel Schillinger, LLP

(57)          ABSTRACT

A system for respiration comprises a respirator, input unit, and telemonitoring unit. The respirator comprises a sensor unit which comprises sensors whose measured values permit an ascertainment of pressure and/or flow and/or volume of supplied and/or exhaled gases, a preparation unit which prepares acquired measured values, a computation unit which determines signals and/or characteristic variables based on the measured values, a recognition unit which uses the values for further analysis, a storage unit which stores these values, and a communication unit. The input unit is configured to provide values and items of information of the user input by a user via the input unit on his health state to the system. The communication unit transmits the values automatically according to one or more permanently programmed and/or freely input time intervals to the telemonitoring unit, which is configured to receive, store, analyze, and/or judge the transmitted values and/or items of information of the respirator and the input unit.

9 Claims, 2 Drawing Sheets

(56) References Cited

U.S. PATENT DOCUMENTS

| | | | |
|---|---|---|---|
| 2015/0133809 A1* | 5/2015 | Paul | A61M 16/0003 |
| | | | 128/205.25 |
| 2016/0364614 A1 | 12/2016 | Silberschatz et al. | |
| 2018/0082033 A1 | 3/2018 | Kent et al. | |
| 2018/0184945 A1* | 7/2018 | Borel | A61M 16/0051 |

* cited by examiner

| Patient: | Illness: | Ventilation: | Overall judgment: |
|---|---|---|---|
| Mustermann, Karl-Heinz | COPD | prismaVENT, mode: S/T | 80% |
| 02.20.1965, ID 4711 | risk level: 3 | nasal mask Joyce One | |

| Category | Judgment | Reasoning |
|---|---|---|
| Usage of respirator: | 100% | daily use >5 hours no unused days |
| Leak-tightness of respiratory mask and mouth | 85% | leakage increased to 15% of the days |
| Function/configuration of the respirator | 79% | AHI elevated-> EPAP possibly too low indication of asynchrony patient complains of dry mouth |
| Stability of respiration/illness, safety from exacerbation/decompensation | 62% | respiratory frequency strongly increased for 3 days irregular breathing for 2 days |

Fig. 2

TELEMONITORING IN RESPIRATION

CROSS-REFERENCE TO RELATED APPLICATIONS

The present application claims priority under 35 U.S.C. § 119 of German Patent Application No. 102018007256.9 filed Sep. 14, 2018, the entire disclosure of which is expressly incorporated by reference herein.

BACKGROUND OF THE INVENTION

1. Field of the Invention

The invention relates to a system for respiration.

2. Discussion of Background Information

Conventional devices for respiration typically comprise a display, to display specific current items of information for the user. In the simplest case, parameters of the respiration, such as current flow or pressure of the respiratory gases, are displayed in the form of numeric values or in the form of graphic representations. In addition, other optical display options such as bar graphs are known for displaying parameters.

Moreover, devices for respiration are known in the prior art, in which parameters are analyzed inside a respirator and displayed to the user on the respirator. Storing parameters and/or measured values, for example, in an internal storage in the respirator or on a USB stick connected to the respirator is also known, so that the measured values can be relayed to a caregiver on the storage device. Optionally, measured values can also be transmitted to a cloud memory for storage.

However, the devices known in the prior art for respiration have the disadvantage that only the user has an analysis of the acquired measured values displayed, and only on the respirator. However, since a user cannot perform a judgment of the displayed and/or analyzed measured values, poor measured results are only apparent by way of a viewing of the values stored on the USB stick or in the cloud by the caregiver, when they are on location. As a result, a user is possibly poorly treated over a long period of time.

In addition to the monitoring of the measured values, the monitoring of the functions and settings of the respirator is also made more difficult. Since the user cannot draw any inferences about poor settings on the respirator based on the analyses, he is reliant on a judgment of the analyses and on a setting of the respirator based thereon by a caregiver. Since the caregiver is only on location at time intervals, however, they can only then perform changes on the settings of the respirator to be able to act on the quality of the treatment of the user.

Furthermore, the analyses of the previously known devices are solely based on measured values acquired by a respirator or on data input by the user via a display screen, for example, age and weight. A consideration of further personalized data, measured values, and items of information, in particular items of medical technical information and measured values acquired by a physician or comparison values have remained unconsidered in the analyses and/or evaluations up to this point.

In view of the foregoing, it would be advantageous to have available a system for respiration which improves the monitoring and quality of respiration.

SUMMARY OF THE INVENTION

The present invention provides a system for respiration comprising at least one respirator, at least one input unit, and at least one telemonitoring unit. The at least one respirator comprises at least one sensor unit, a preparation unit, a computation unit, a recognition unit, a memory unit, and a communication unit. The sensor unit comprises sensors, the measured values of which permit an ascertainment of pressure and/or flow and/or volume of the supplied and/or exhaled gases. The preparation unit prepares the acquired measured values, the computation unit determines signals and/or characteristic variables based on the measured values, the storage unit stores these values, and the recognition unit uses the values for further analyses. The input unit is configured to provide values input by a user of the system via the input unit and items of information of the user on his health status to the system, and the communication unit transmits the values to the telemonitoring unit.

All measured values, signals, characteristic variables, and items of information are summarily referred to values.

The preparation unit of the respirator is configured to prepare the measured values acquired by the sensors of the sensor unit. A preparation can be in this case a smoothing, a statistical evaluation, a determination of a minimum or a maximum, a mean and/or median, a percentile, and the recognition of patterns or an overshoot/undershoot of limiting values. Further signal preparations are, for example, clocking down or filtering artifacts.

The computation unit of the respirator is configured to ascertain signals and/or characteristic variables from the prepared measured values. A characteristic variable can be, for example, a mean value, a median, a percentile, a derivative, a frequency distribution, a duration, or a proportion of the overshoot or undershoot of a threshold value. The computation unit is configured to transmit the prepared and computed characteristic variables to the recognition unit, wherein the recognition unit is configured to recognize events and/or states. Such events can be breathing interruptions, artifacts, coughs, oxygen desaturation, asynchrony between respirator and patient, inhalation, exhalation, mandatory breaths, or alarms.

The storage unit of the respirator is configured to temporarily store the measured values acquired by the sensors of the sensor unit, the prepared measured values, signals, characteristic variables, and the events and states which were acquired by the recognition unit.

The communication unit of the respirator is configured to transmit the measured values, signals, and characteristic variables temporarily stored in the storage unit to the telemonitoring unit.

The respirator can optionally comprise a monitoring unit, which is configured to recognize technical problems. Technical problems can be in this case, inter alia: a low battery level, faults in the electronics, a defective battery, a defective component, a power failure, an incorrectly functioning accessory part, an implausible measured value, or leaving the permitted temperature range. The monitoring unit of the respirator can be configured to output an alarm upon a recognition of a technical problem, which is displayed to the user/patient on the respirator.

In general, the respirator moreover comprises at least one pressure generating unit and a patient interface.

According to the invention, the telemonitoring unit is configured to receive, store, analyze, and/or judge the transmitted values and/or items of information of the respirator and the input unit of the respirator. The transmission of the measured values and/or items of information can optionally be configured as time-controlled, manually triggered (for example, triggered on the home treatment devices or on the server), event-controlled (for example, upon recognition of specific critical states by the treatment device), or as a continuous transmission, at least during a running treatment. A transmission of the measured values, signals, characteristic variables, and/or items of information of the user preferably takes place about every 2 hours to 7 days, in particular about every 1 to 3 days. In one preferred embodiment, the transmission takes place at least once per day/per 24 hours. Alternatively, the communication unit of the respirator can be configured to transmit the values in summary every hour or to transmit the measured values in real time. The transmission cycle is optionally freely selectable by the user and/or by the caregiver. The communication unit of the respirator can be configured to carry out the transmission independently, possibly repeatedly or continuously, after one or more fixedly programmed and/or freely input time intervals. Optionally, it is additionally analyzed whether a data transmission has successfully taken place, whether it has regularly taken place, and/or whether it occurred without error.

In the case of a failure of a data connection, the storage unit of the respirator is configured to store the measured values and/or the items of information from the input unit for at least one day, wherein the communication unit of the respirator is configured to transmit the measured values to the telemonitoring unit, as soon as a data connection has been established again.

In general, the items of information of the user and the measured values acquired by the sensors of the respirator are compiled in the telemonitoring unit. The communication unit of the respirator can optionally be configured to compile the items of information and values of the user and the measured values, characteristic variables, and signals of the respirator already in the respirator and then to transmit them together to the telemonitoring unit.

The telemonitoring unit thus offers the advantage that the values and items of information of the respirator and of the input unit can be combined and analyzed together in the telemonitoring unit. The input unit can be designed as a component of a human-machine interface of the respirator, software for a smart phone, a tablet, or a PC, software for a speech assistant, or as an independent electronics unit having a human-machine interface. Via the input unit, a user can thus introduce values and items of information on his health state into the system according to the invention for the respiration. The input unit can therefore be formed externally from the respirator. Alternatively, the input unit is formed in or on the respirator. This offers the advantage that the values and items of information on his person are introducible directly by the user into the system. The analysis of the acquired measured values, signals, and/or characteristic variables can thus be performed based on additional measured values of the user and/or based on items of information on the general health status of the user.

The input unit is typically configured to transmit the values and/or items of information input by the user on his health state alternately to the respirator and/or to the telemonitoring unit.

The input unit can be formed separately from the respirator. Due to the separate arrangement, a spatial proximity of the user to the respirator is not required for the input of values and/or items of information.

The measured values ascertained in the respirator and the values and/or items of information input via the input unit into the system can be transmitted separately from one another to the telemonitoring unit. Alternatively, the input unit can be configured to firstly transmit the measured values and items of information to the respirator, wherein the values and/or items of information are then transmitted via the respirator to the telemonitoring unit.

The telemonitoring unit is typically arranged externally from the respirator. Due to the external storage, analysis, and judgment of the values and/or items of information, the values, analyses, and judgments of the telemonitoring unit can be accessed independently of location. Due to the external arrangement, the telemonitoring unit is configured to receive items of information both from the respirator and also from an optional externally arranged input unit.

The telemonitoring unit can furthermore be configured to relay the analyzed and/or judged values to a caregiver. This offers the advantage that it is made possible by means of the telemonitoring unit to digitally transmit the measured values acquired by the respirator, which were prepared, computed, and analyzed and possibly compared to values and/or items of information which were introduced by the user via the input unit into the system, to a caregiver, preferably an attending physician. This enables monitoring of measured values and the function of the respirator, and of the state of the user by a physician who is not present on location. For example, the physician can thus, if a worsening of the measured values is established or possibly as a result of output alarms, actively give feedback to the user, for example, the physician can contact the user via a direct communication channel, for example, via telephone.

In one embodiment, the telemonitoring unit comprises a communication unit, a storage unit, at least one analysis unit, at least one output unit, a judgment unit, and at least one information unit.

The communication unit of the telemonitoring unit is configured as a buffer for communication with a plurality of respirators. The communication unit is configured to receive measured values and information from at least one respirator and/or at least one input unit.

Optionally, the communication unit of the telemonitoring unit can be configured to receive measured values and/or items of information of an additional measuring unit or an additional telemonitoring unit.

The storage unit of the telemonitoring unit is configured to store the values received by means of the communication unit and values which are provided to the system via the information unit and possibly to perform an assignment of a device to its patient, for example, via a name of the patient, an ID, or a serial number. The storage unit is thus configured to at least temporarily store the measured values and items of information ascertained by the additional measuring unit and the additional telemonitoring unit, the input unit, and by the respirator. The storage unit is configured to provide the stored values to at least one analysis unit.

An analysis unit is preferably configured in each case for at least one question. For example, the following questions can be answered: Is the respirator sufficiently used? Is the leak-tightness of mouth and patient interface sufficient? Does the respirator function correctly? Are the configurations/settings on the respirator correctly selected? Is the illness state stable without indication of an exacerbation/decompensation? The questions are freely selectable and can be supplemented by further questions. A selection of questions is typically stored in the telemonitoring unit, wherein the questions to be evaluated by analysis units can be freely compiled by a caregiver depending on the user. The analysis is preferably carried out on the basis of rules, threshold values, or artificial intelligence. In this case, a weighting of the received items of information is performed depending on the question. The analysis units can be configured to weight values depending on source location, for example, originating from the caregiver or the user. Alternatively, the analysis units can be configured to weight the questions according to storable rules.

In one preferred embodiment, the system according to the invention comprises at least four analysis units, wherein each of the analysis units represents one question. The preset logics of the questions in the respective analysis units are modifiable.

In general, an output unit is configured in each case to output a result for a question analyzed by the analysis unit. The result can preferably be displayed in the form of a characteristic number or a graphic and/or by color differentiation. The result is preferably output as fulfilled or unfulfilled and/or good or poor. The telemonitoring unit typically comprises at least two analysis units. A recognition report of suboptimal settings of the respirator or respiration situations which can negatively influence the treatment quality can be performed via the output units. For example, an item of information about a poor trigger setting/asynchrony, an item of information about air traps, for example, about an intrinsic PEEP in the case of an analysis of the flow curve, an item of information about a strong secretion formation, for example, windy flow courses or the frequency of coughs, an item of information about an irregularity or unreasonable usage patterns of respiration programs or special functions, an item of information about the aging of the battery, or an item of information about incorrectly connected accessories can be output via the output unit. The telemonitoring unit preferably comprises a number of output units in each case which corresponds to the number of analysis units. In one advantageous embodiment, the telemonitoring unit comprises four analysis units and four corresponding output units.

The judgment unit is generally configured to output an overall judgment for a patient based on the results ascertained by the output units for a user. The overall judgment is configured to output an overall judgment of the health state of the user on the basis of the results output by the output units. The overall judgment can be represented on the basis of the number of possible problems. In the case of a critical overall judgment, active messaging of the caregiver can take place via chat, email, SMS, or telephone call.

The judgment unit is configured to output a prediction about the course of the measured values, the health state, or possibly occurring complications based on at least one fulfilled question. In one advantageous embodiment, a prediction about the health state or occurring complications is output based on at least two questions judged to be fulfilled. For example, a prediction on the health state can be output if at least two of four questions are output as fulfilled. Optionally, a prediction can also be performed for further categories. For example, a prediction can be output with respect to a parameter, for example, a temperature profile. A prediction can also be, for example, an item of information about increasingly faster and shallower breathing, which is ascertained, for example, from trends of the tidal volume, the respiratory frequency, the alveolar tidal volume, or the rapid shallow breathing index. Alternatively, the judgment unit is configured to output a prediction about the course of the measured values, the health state, or possibly occurring complications based on at least one unfulfilled question. In general, the output of the prediction can be selected based on being fulfilled or unfulfilled.

The judgment unit is configured to output an alarm based on the prediction, for example, a complication. The judgment unit is preferably embodied as a human-machine interface (HMI). An output alarm can be transmitted visually and/or acoustically via the HMI. For example, the HMI can output a display screen, an SMS or email, a 3D screen, data spectacles, or a projection. The HMI can moreover output an automatic telephone call function or speech statement. Due to the design of the judgment unit as an HMI, an alarm can be transmitted to the caregiver in the event of a negative prediction. Optionally, the judgment unit is also active if the respirator is not treating or is switched off. In general, the logic of the judgment unit is configured as modifiable, wherein an engagement in the respirator is omitted. For example, a configuration or an update of the judgment unit can thus be carried out independently of the respirator.

The information unit is generally configured as an access point for the supply of additional items of information about the user by the caregiver into the telemonitoring unit of the system. For example, items of information on the illness type, the risk class, or the anamnesis for the analysis can be introduced via the information unit into the telemonitoring unit. In general, all items of information exchanged via the direct communication channel can be introduced into the system and/or transmitted to the telemonitoring unit by the information unit.

In one embodiment, the information unit is configured as a data input. By way of the information unit, values on the state of the user are introducible into the telemonitoring unit, wherein the values are stored in the storage unit of the telemonitoring unit. The information unit can be designed as a digital interface, for example, as a software application which can be executed on a computer or a tablet or smart phone. The information unit can be designed as an HMI. The information unit can be embodied as an input display screen or as an acoustic query. For example, items of information about answers of the user to standardized questionnaires, for example, on difficulty breathing, quality-of-life, and exacerbation risk can be introduced via the information unit. Therefore, items of information of a caregiver in the form of an electronic log can also be introduced into the system by means of the information unit.

A caregiver, for example, a physician, can also input his current items of information about the user and/or values of a visit via the information unit into the telemonitoring unit to base the analyses of the analysis units on the current items of information. The information unit thus offers the option of carrying out analyses which are carried out in the telemonitoring unit in a manner personalized to a user and to also take into consideration the personalized current aspects of a patient during the analysis in each case.

In a further embodiment, the telemonitoring unit is designed as a combination interface which is configured to combine values and/or items of information transmitted via the information interface to the telemonitoring unit, values and/or items of information transmitted via the input unit, and values and/or items of information transmitted via the respirator to the telemonitoring unit and base a further analysis and/or judgment thereon. Values and/or items of information from an external data source can be in this case, for example, values with respect to $CO_2$, for example, $ptCO_2$, $SpO_2$, $FiO_2$, values from the insufflator/exsufflator, and also blood gases or blood values (markers). The embodiment of the telemonitoring unit as a communication interface offers the advantage that measured values and/or items of information of various sources can be compiled, wherein the sources can be spatially and/or positionally separated from one another. Values and items of information can originate in this case from users, caregivers, and/or external data sources. The compiled items of information can be used as the basis of analyses. Analyses which are based on the compiled values and/or items of information of the various sources enable an accurate and personalized analysis by the incorporation of a plurality of different values.

In one embodiment, the telemonitoring unit is an external server. The embodiment of the telemonitoring unit as an external server offers the advantage that both a user and also a caregiver can each access the telemonitoring unit and can store items of information, so that personalized analyses and judgments can be carried out without the user and/or the caregiver having to perform the access directly at the respirator.

In a further embodiment, the input unit is formed on the respirator or as an external terminal. The input unit can be formed integrated into a display screen of the respirator or can be configured as software in an application in this case. The input unit configured as a software application can be executed, for example, on tablets, smartphones, or computers. The embodiment of the input unit as an application is particularly advantageous, since a patient, without approaching the respirator, can check his health state and the configuration of the respirator via a smart phone and can possibly perform settings which are displayed by the telemonitoring unit on the basis of the analysis and judgment.

In one refinement, the information unit is configured to acquire external comparison values and/or items of information from external data sources. For example, the information unit can be configured to check general items of information with respect to a clinical picture from a database and provide them to the system according to the invention. External comparison values and/or items of information can be in this case comparison measured values for the measured values acquired by the respirator, side effects, or further items of background information of corresponding clinical pictures.

In one further refinement, the at least one analysis unit of the telemonitoring unit is configured to combine and analyze the values of the user and values about the user stored in the storage unit, wherein the combined values and items of information are related to at least one question, wherein fulfilling at least one question provided in a defined period of time is at least temporarily acquired as a procedure and output via the at least one output unit.

This offers the advantage that both current items of information about the perceived and measured state of the user and also items of background information and/or technical information of a caregiver can be used for the analysis and judgment of the measured values ascertained by the respirator and of the ascertained health state of the user.

In one embodiment, at least one output unit is configured, upon fulfillment of the at least one question, to transmit a corresponding alarm, preferably optically and/or acoustically, to the input unit on the respirator and/or to a terminal and/or to effectuate a change of the operating mode of the respirator, in particular the parameters, using which the respirator carries out the ventilation. It can be selected in this case whether an alarm is to be output if a question is fulfilled or not fulfilled. For example, a corresponding alarm can take place if the question "is the respiration mask seated correctly?" is displayed as not fulfilled. In this case, an alarm can be transmitted to the respirator or to the input unit, so that the user can perform a correction of the seat of the mask.

The alarm can optionally be accompanied by instructions for improvement, for example, of the position of the respiration mask.

In one refinement of the invention, the judgment unit of the telemonitoring unit is configured to ascertain an overall criticality of a health state of the user from at least two fulfillments output by the output units and to output an alarm in dependence on the ascertained overall criticality. The judgment unit can optionally be configured to ascertain an overall criticality for the quality of the health state of the user based on output "non-fulfillments". An overall criticality can be stored in this case by permanently stored formulas, for example, as a total score or max score for problems. Optionally, stored formulas can be configured as selectable and configurable. In addition, the formulas can be weighted by inputs of the caregiver and/or user on the patient type (for example, illness and severity).

In one embodiment of the refinement, the judgment unit is configured to output a prediction with respect to the health state of the user or possible complications based on the fulfillments of the output unit. Alternatively, the prediction can be based on output "non-fulfillments". The logic of the prediction can generally be modifiable in this case by manual change of the threshold values or by automatic learning on the basis of data from the past. The judgment unit can optionally be configured to alarm a caregiver assigned for the respective prediction depending on the output prediction. In a further embodiment, a current caregiver can be stored in the judgment unit.

The invention furthermore provides a method for the display or control for a system for respiration according to any one of the above-described features, in which measured values are ascertained in a respirator by at least one sensor of a sensor unit, which permit an ascertainment of pressure and/or flow and/or volume of the supplied and/or exhaled gases, wherein these measured values are prepared via a preparation unit, supplied for further computations to a computation unit, and supplied in a further step for further analyses to a recognition unit, where the system transmits the computed and analyzed measured values to a telemonitoring unit, and in which items of information on the health state of his person are storable by a user via an input unit of the respirator, wherein these items of information are transmitted to the telemonitoring unit.

According to the invention, the telemonitoring unit relates the measured values, signals, and characteristic variables transmitted by the communication unit of the respirator to items of information on the health state of the user and/or external comparison values stored via an information unit of the telemonitoring unit by a caregiver and checks them with respect to at least one question. The telemonitoring unit transmits values from the respirator, from the input unit, from an additional measuring unit, from an additional telemonitoring unit to a communication unit of the telemonitoring unit, wherein the transmitted values are temporarily stored in a storage unit and relayed to at least one analysis unit, which is formed in the telemonitoring unit. The at least one analysis unit checks the transmitted values with respect to at least one question.

In one embodiment, at least one output unit outputs a corresponding alarm and/or a corresponding display upon fulfillment of at least one question represented by at least one analysis unit. Alternatively, a corresponding alarm can be output by the at least one output unit upon non-fulfillment of the question.

In a further embodiment, the caregiver receives, upon fulfillment of at least one question, an item of information about which question was fulfilled and/or which parameter has a deviation from the target value and/or which of the settings pressure, flow, volume, time, frequency would have to be adapted to come back into a predetermined target value range. The item of information is preferably transmitted via the judgment unit to the caregiver. Alternatively, the caregiver can receive, upon non-fulfillment of at least one question, an item of information about which question was fulfilled and/or which parameter has a deviation from the target value and/or which of the settings pressure, flow, volume, time, frequency have to be adapted.

In one refinement of the method, the items of information about the target value deviation and/or a fulfilled question are stored together with recommendations with respect to the required adaptation of one or more parameters in the respirator and are retrieved therein by the user and are also automatically executed upon selection or transmitted via the judgment unit of the telemonitoring unit to the caregiver. Optionally, required settings can be carried out on the respirator via a remote transmission by the caregiver based on the items of information output to the caregiver.

In one embodiment, a judgment unit of the telemonitoring unit ascertains, from the fulfilled questions, a prediction with respect to the health state of the user and/or complications. For example, a prediction on the health state can be output if at least two of four questions are output as fulfilled. Optionally, a prediction can also be performed for further categories. A prediction can be, for example, an item of information about increasingly faster and shallower respiration. Alternatively, the evaluation unit outputs, based on at least one unfulfilled question, a prediction about the course of the measured values, the health state, or possibly occurring complications. In general, the output of the prediction is selectable based on a fulfillment or non-fulfillment.

Optionally, the items of information about the target value deviation and/or fulfilled question are also transmitted together with recommendations with respect to the required adaptation of one or more parameters from the respirator via remote transmission (Internet, radio, cable, inter alia) to a physician, whereupon this physician optionally also adapts the required settings of the parameters via a remote transmission.

The present invention furthermore provides a respirator comprising a system for respiration according to any one of the above-mentioned features.

BRIEF DESCRIPTION OF THE DRAWINGS

Preferred exemplary embodiments of the invention are explained in greater detail hereafter on the basis of greatly simplified schematic illustrations. In the drawings:

FIG. 2 shows an illustration of one embodiment of a reproduction of a display.

Figure 1:
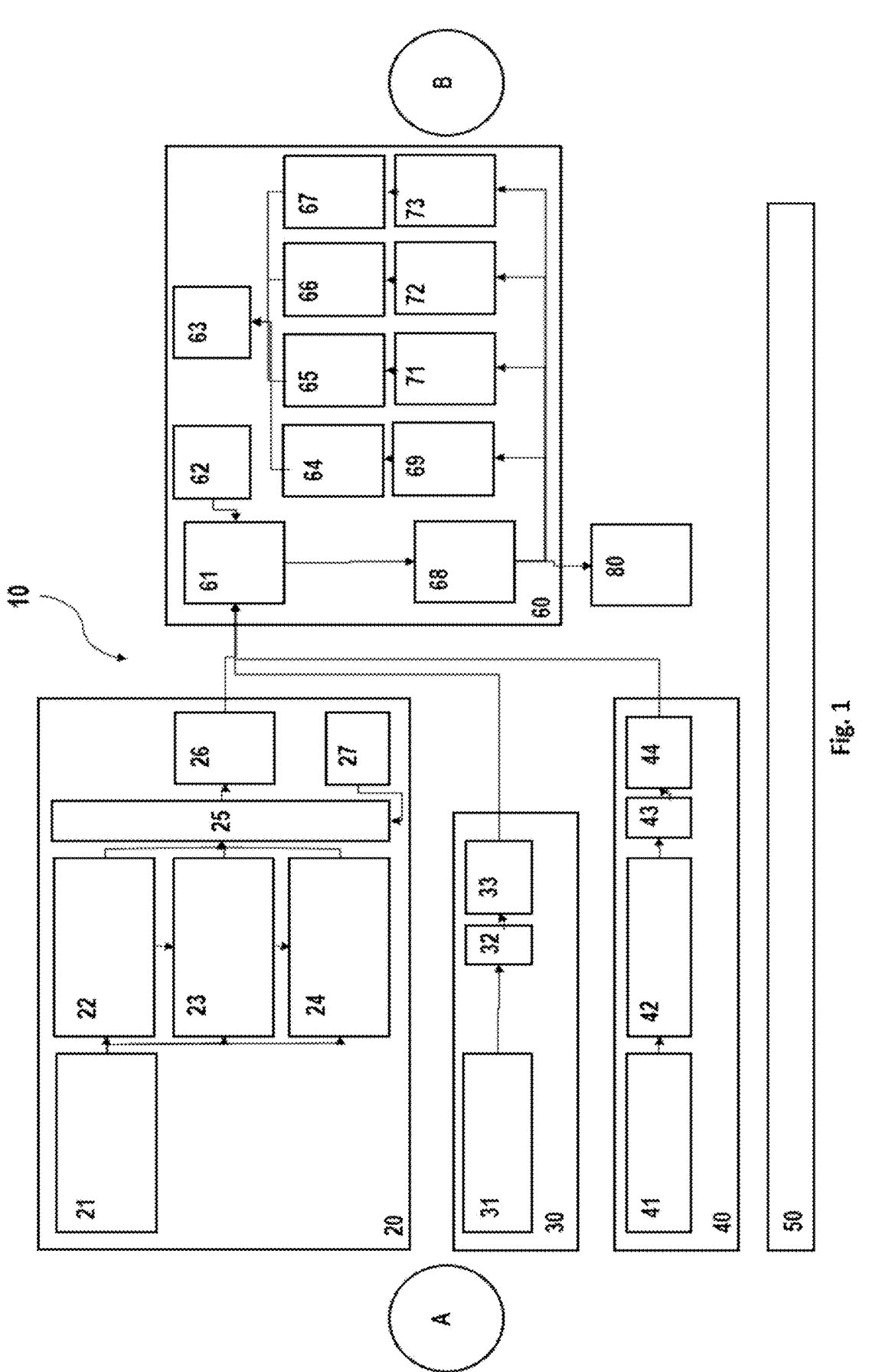
FIG. 1 shows one embodiment of a design of the system according to the invention for respiration.

In the drawings, the same constructive elements have the same reference signs in each case.

DETAILED DESCRIPTION OF EXEMPLARY EMBODIMENTS

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show details of the present invention in more detail than is necessary for the fundamental understanding of the present invention, the description in combination with the drawings making apparent to those of skill in the art how the several forms of the present invention may be embodied in practice.

One embodiment of the system for respiration 10 according to the invention is illustrated in FIG. 1.

The system 10 according to the invention comprises in this exemplary embodiment a respirator 20 and an input unit 30, an additional measuring unit 40, a direct communication channel 50, a telemonitoring unit 60, and an additional telemonitoring unit 80.

The system 10 according to the invention is configured to facilitate and improve the communication between a user A and a caregiver B and to improve the quality of the respiration therapy. A caregiver can be, for example, a physician, a therapist, a home care provider, a nurse, or a relative.

In the present embodiment, the respirator 20 comprises a sensor unit 21, a preparation unit 22, a computation unit 23, a recognition unit 24, a temporary storage unit 25, a communication unit 26, and a monitoring unit 27.

The sensor unit 21 is configured to acquire measured values, in particular parameters, which are related to a respiratory flow, a respiratory volume, a respiratory frequency, an inhalation and exhalation duration, a respiratory contour, a leak, or a treatment pressure. The sensor unit 21 can optionally perform additional measurements of components or temperature of the respiratory gas or of the blood. The sensor unit 21 transmits the acquired measured values to the preparation unit 22.

The preparation unit 22 can prepare the acquired measured values. For example, the preparation unit can carry out a smoothing, a filtering of artifacts, or a down-sampling of the measured values. The preparation unit transmits the prepared measured values to the computation unit 23.

The computation unit 23 computes, from the measured values acquired by the sensor unit 21 and prepared by the preparation unit 22, signals and/or characteristic variables, for example, a mean value, a median, a percentile, a derivative, a frequency distribution, a duration, or a proportion of an overshoot or undershoot of threshold values. The computation unit 23 transmits the computed measured values, signals, and characteristic variables to the recognition unit 24.

The recognition unit 24 is configured to recognize events/ states such as alarms, respiratory interruptions, artifacts, coughs, oxygen desaturation, asynchrony between device and user, inhalation, exhalation, or mandatory breaths.

The temporary storage unit 25 is configured to temporarily store the signals and/or characteristic variables computed by the computation unit 23 and/or the events recognized by the recognition unit 24. The temporary storage unit 25 advantageously stores the stored items of information at least up to a next communication procedure between the communication unit 26 of the respirator 20 and the telemonitoring unit 60. The communication unit 26 is, for example, one of the following mentioned communication systems: GSM, Lora, LPWAN, NB-IOT, LTE-M, LTE, UMTS, LAMN WIFI, WLAN, Bluetooth.

Moreover, the monitoring unit 27 can record technical problems of the respirator 20. Technical problems can be, for example, a low battery level, faults in the electronics, a defective battery, a defective component, a power failure, an incorrectly functioning accessory part, an implausible measured value, or leaving a permitted temperature range. The monitoring unit 27 can display an alarm on the respirator or transmit it via the telemonitoring unit 60 to the caregiver if a technical problem is recognized.

The input unit 30 of the system for respiration 10 is a human-machine interface 31, which enables an input of measured values and/or items of information of a user to the respirator. For example, a user can thus introduce information of other measuring devices, for example, a temperature measured by means of a thermometer or a pulse acquired by means of a pulse measuring device into the system 10. The measured values and/or items of information thus introduced can be transmitted directly by the input unit 30 or by the respirator 20 to the telemonitoring unit 60 and used therein for analyses.

The input unit 30 moreover comprises a temporary storage unit 32 and a communication unit 33. The temporary storage unit 32 stores the items of information input by the user in the input unit 30. The communication unit 33 is designed similarly to the communication unit 26 in the respirator. The communication unit 33 transmits the input values to the telemonitoring unit 60. Alternatively to a direct communication with the telemonitoring unit 60, the transmission of the values can firstly take place to the respirator 20. For example, this communication between the input unit 30 and the respirator 20 can take place via a cable or Wi-Fi or Bluetooth. The communication unit 33 can relay the temporarily-stored values of the input unit 30 in bundles or continuously to the telemonitoring system 60 or the respirator 20.

The present embodiment of the system 10 according to the invention for the respiration moreover contains an additional measuring unit 40, which comprises a sensor unit 41, a processing unit 42, temporary storage 43, and a communication unit 44. The additional measuring unit 40 can optionally be formed in the system 10 according to the invention for the respiration. In an alternative embodiment, the system 10 according to the invention can dispense with an additional measuring unit 40. The additional measuring unit 40 can be, for example, a measuring device for acquiring oxygen, an oxygen saturation in the blood, respiratory gases, $CO_2$ in the blood, a blood pressure, a heart rate, coughing, secretion, body temperature, weight, or an activity. The additional measuring unit 40 preferably comprises in this case a sensor unit 41, wherein the sensor unit 41 is at least one sensor, for example, for acquiring $O_2$, $SpO_2$, $CO_2$, temperature, weight, heart rate, coughing, respiratory gases, blood pressure, or activity. The additional measuring unit 40 can also be an activity measuring device, a sleep quality measuring device, or a lung function measuring device. The processing unit 42 processes the ascertained measured values, for example, by down-sampling, smoothing, or artifact recognition, computation of statistical characteristic numbers or by recognition of states and events. The temporary storage 43 stores the processed measured values. The measured values ascertained by means of the additional measuring unit 40 can be transmitted via the communication unit 44 to the telemonitoring unit 60 and further analyses can be based thereon. The communication unit 44 is designed similarly to the communication unit 26 of the respirator 20. The communication unit 44 can transmit the processed measured values, for example, via GSM, Lora, LPWAN, NB-IOT, LTE-M, UMTS, LAN, WIFI, WLAN, or Bluetooth to the telemonitoring unit 60. Alternatively to a direct connection to the telemonitoring unit 60, a communication with the respirator 20 can also take place, for example, via a cable, Wi-Fi, or Bluetooth. In this case, the items of information are transmitted further in bundled form to the telemonitoring unit 60.

The system for respiration 10 can also comprise a direct communication channel 50. The direct communication channel 50 can take place, for example, via speech or video and can be used for a query of a set of symptoms. Complaints, a quality of life, risk scores, side effects, questions on the treatment, clarification of handling difficulties, and instructions in the case of problem situations or manual emergency alarms can be transmitted between user and caregiver via the direct communication channel 50. The items of information from the direct communication channel 50 can be input into the telemonitoring unit 60 and used for further analyses.

The telemonitoring unit 60 of the system 10 comprises a communication unit 61, an information unit 62, a judgment unit 63, output units 64, 65, 66, 67, a storage unit 68, and analysis units 69, 71, 72, 73.

The communication unit 61 functions in the present embodiment as a buffer for communication with a plurality of respirators. The communication unit 61 receives the measured values transmitted by the respirator 20, the input unit 30, and the additional measuring device 40.

The storage unit 68 is configured to at least temporarily store the values transmitted via the communication unit 61 to the telemonitoring unit 60. Furthermore, the storage unit 68 can carry out an assignment of a user to a device, for example, via the name of the user, an ID, or a serial number.

The information unit 62 is configured as a data input and enables an input of additional values and items of information by the caregiver. For example, items of information on illness types, items of information on a risk class, items of information on anamnesis, and also all items of information exchanged via the direct communication channel 50 can be introduced into the telemonitoring unit 60 and also transmitted like intervention protocols. In accordance with the items of information on illness types, items of information on a risk class, and items of information on anamnesis, different specific analysis rules can apply in each case and can be provided and applied (by the analysis unit).

Additional items of information and measured values about the user can be introduced by the caregiver into the system via the information unit 62, to take them into consideration during the analysis. For example, items of information about an illness type, a risk class, or anamnesis can be introduced via the information unit. In general, any items of information which can also be exchanged, for example, via a direct communication channel 50 or intervention protocols can also be provided via the information unit to the telemonitoring unit 60 for further analysis.

The analysis units 69, 71, 72, 73 are configured to execute analyses with respect to at least one question. Possible questions can be in this case whether the respirator is sufficiently used, whether there is sufficient leak-tightness of mouth and patient interface/respiration mask, whether the respirator is correctly functioning and configured and/or whether the settings of the respirator are correct, whether the illness state is stable without indication of an exacerbation/decompensation. For each question, an indicator can be used, for example, "good" or "poor", 0 and 100% problem severity, 0 and 100% therapy quality, or 3-5 categories, for example, "very good", "good", "moderate", "poor", and "very poor". Optionally, the indicators about all questions can be added/combined in a further step. This offers the advantage that users having multiple "problems" can be displayed separately from users of one "problem". A weighting of the problems can optionally be performed.

The output units 64, 65, 66, 67 are configured to enable the output of analysis results of the at least two analysis units, for example, in the form of a characteristic number or a graphic and color differentiation of at least good and poor results.

The judgment unit 63 ascertains based on the number of the results output by the output unit an overall judgment about the health state of the user. Optionally, active messaging of the caregiver can be performed via chat, email, SMS, telephone call, or via a further communication path.

Furthermore, the judgment unit 63 ascertains, based on at least one question judged as fulfilled or not fulfilled of the output unit 64, 65, 66, 67, a prediction about the course of the measured values, the health state of the user, or possibly occurring complications. For example, a prediction about the health state or occurring complications is output based on at least two questions judged as fulfilled. Alternatively, the judgment unit 63 is configured, based on at least one unfulfilled question, to output a prediction about the course of the measured values, the health state, or possibly occurring complications. In general, the output of the prediction is selectable based on a fulfillment or non-fulfillment.

The judgment unit 63 can output an alarm based on the prediction, for example, a complication. The judgment unit 63 is preferably embodied as a human-machine interface (HMI). An output alarm can be transmitted visually and/or acoustically via the HMI. The HMI can moreover output an automatic telephone call function or speech statement. By way of the embodiment of the judgment unit 63 as an HMI, an alarm can be transmitted to the caregiver in the event of a negative prediction.

In the present exemplary embodiment, the system 10 moreover comprises a further telemonitoring unit 80. The further telemonitoring unit 80 can comprise, for example, a server having software for linkage to further items of information. The communication can take place, for example, via API, SFTP, https, or files. Other communication paths are also compatible/usable. The values of the additional telemonitoring unit 80 are transmitted to the telemonitoring unit 60 and further analyses are based thereon.

An embodiment of an exemplary display is shown in FIG. 2. Such a display can be displayed, for example, on the respirator or a terminal. In this case, for example, the patient is identified by name, year of birth, and/or ID. Moreover, specifications can be displayed with respect to the illness, for example, a COPD illness, and a risk level. Moreover, it can be displayed in which form and in which mode the patient is presently being respired, using which device and using which accessory material. Furthermore, various categories, judgments on these categories, and an additional reasoning can be displayed. Examples of a category can be the usage of the respirator, the leak-tightness of respiration mask and mouth, a function/configuration of the respirator, or a stability of the respiration/illness and/or a safety from exacerbation/decompensation. The above-mentioned categories can be represented via the judgment. In this case, for example, a classification of 0-100% can be displayed. Additional items of auxiliary information can be displayed to the user and/or the caregiver in the reasoning. Furthermore, in the present exemplary embodiment of an exemplary display, an overall judgment is indicated. In the present case, the overall judgment is indicated, for example, as 80%. The overall judgment provides a statement about the overall health state of the user. The graphic representation of the display is variable and can be adapted by a user and/or caregiver. Optionally, further categories can be added to the display in accordance with the user. The judgment can optionally be graphically displayed. In general, the display moreover comprises, in the case of output of a fulfillment or non-fulfillment of a question by the output unit—shown in FIG. 1—a prediction with respect to the health state of the user or possible complications occurring in future.

LIST OF REFERENCE SIGNS

A user
B caregiver
10 system for respiration
20 respirator
21 sensor unit
22 preparation unit
23 computation unit
24 recognition unit
25 temporary storage unit
26 communication unit
27 monitoring unit
30 input unit
31 human-machine interface
32 temporary storage unit
33 communication unit
40 additional measuring unit
41 sensor unit
42 processing unit
43 temporary storage
44 communication unit
50 direct communication channel
60 telemonitoring unit
61 communication unit
62 information unit
63 judgment unit
64, 65, 66, 67 output units
68 storage unit
69, 71, 72, 73 analysis units
80 additional telemonitoring unit

What is claimed is:

1. A system for respiration, wherein the system comprises a respirator (i), at least one input unit (ii), and at least one telemonitoring unit (iii), wherein the respirator (i) comprises at least one sensor unit (iv), a preparation unit (v), a computation unit (vi), a recognition unit (vii), a storage unit (viii), and a communication unit (ix), wherein the sensor unit (iv) comprises sensors, measured values of which permit an ascertainment of pressure and/or flow and/or volume of supplied and/or exhaled gases, the preparation unit (v) prepares acquired measured values, the computation unit (vi) determines signals and/or characteristic variables based on the measured values, the storage unit (viii) stores the measured values, and the recognition unit (vii) uses the measured values for further analysis, wherein the at least one input unit (ii) is configured to provide values of a user (A) and items of information of the user (A) via user (A) input on the health state of the user (A) to the system, wherein the communication unit (ix) transmits the measured values, signals and/or characteristic variables to the at least one telemonitoring unit (iii), and wherein the at least one telemonitoring unit (iii) is configured to receive, store, analyze, and/or judge the transmitted measured values, signals and/or characteristic variables and/or items of information of the respirator (i) and the at least one input unit (ii), wherein the at least one telemonitoring unit (iii) is designed as a combination interface that is configured to combine values and/or items of information transmitted via an information interface configured as access point for inputting additional information about the user by a caregiver to the at least one telemonitoring unit (iii), values and/or items of information transmitted via the at least one input unit (ii), and also values and/or items of information transmitted via the at least one respirator (i) to the at least one telemonitoring unit (iii) and base at least one further analysis and/or judgment thereon, wherein the telemonitoring unit (iii) comprises at least one analysis unit which is configured to conduct at least one analysis related to at least a question with respect to a sufficient tightness of the patient interface and wherein the telemonitoring unit (iii) further comprises at least one output unit which is configured, upon non-fulfillment of the at least one question, to transmit a corresponding alarm to the at least one input unit (ii), which alarm is accompanied by instructions to improve a position of the patient interface.

2. The system of claim 1, wherein the at least one telemonitoring unit (iii) further comprises a communication unit, a storage unit, at least one analysis unit, at least one output unit, a judgment unit, and at least one information unit.

3. The system of claim 2, wherein the at least one information unit of the at least one telemonitoring unit (iii) is configured as a data input.

4. The system of claim 2, wherein the at least one information unit is configured to acquire external comparison values and/or items of information from external data sources.

5. The system of claim 1, wherein the at least one telemonitoring unit (iii) is an external server.

6. The system of claim 1, wherein the at least one input unit (ii) is formed on the respirator (i).

7. The system of claim 1, wherein the corresponding alarm is transmitted optically and/or acoustically.

8. The system of claim 1, wherein the corresponding alarm is transmitted at least optically.

9. The system of claim 1, wherein the corresponding alarm is transmitted at least acoustically.

* * * * *